United States Patent [19]
Terhune

[11] Patent Number: 5,373,742
[45] Date of Patent: Dec. 20, 1994

[54] ULTRASONIC INTERFEROMETER

[75] Inventor: James H. Terhune, San Jose, Calif.

[73] Assignee: General Electric Company, San Jose, Calif.

[21] Appl. No.: 11,560

[22] Filed: Feb. 1, 1993

[51] Int. Cl.$^5$ .............................................. G01N 29/00
[52] U.S. Cl. .................................... 73/606; 73/627
[58] Field of Search .............. 73/608, 606, 646, 629, 73/627; 181/206

[56] References Cited

U.S. PATENT DOCUMENTS 3,886,488  5/1975  Bossaert .................................. 367/7
5,271,274  12/1993  Khuri-Yakub et al. ............ 73/629 X

FOREIGN PATENT DOCUMENTS 0236175  of 1987  European Pat. Off. .
0428443  of 1991  European Pat. Off. .
2709686  of 1978  Germany .
2147102  of 1985  United Kingdom .

OTHER PUBLICATIONS

"Fundamentals of Optics" by F. A. Jenkins & H. E. White, 3rd Edition, pp. 244–259 (pre-1976).
"Ultrasonic Testing of Materials" by J & H. Krautkrämer, 4th Edition, pp. 222–224, Springer-Verlag, New York (1990).

Primary Examiner—Richard E. Chilcot, Jr.
Assistant Examiner—Joseph L. Felber
Attorney, Agent, or Firm—J. S. Beulick

[57] ABSTRACT

A method of measuring thin film properties of materials using interference of ultrasonic waves in the frequency range of 2–15 MHz. An ultrasonic interferometer produces interference "fringes" from which the film thickness can be accurately determined. The film may consist of any solid material having known sonic properties and thickness of the order of the sonic wavelength. The device utilizes a narrow-band source of ultrasound and guided-wave propagation to accurately define the optical path of the ultrasonic waves producing the interference. The interferometer is also useful to measure certain material properties in thin specimens, thereby allowing the material to be characterized locally.

20 Claims, 4 Drawing Sheets

ULTRASONIC INTERFEROMETER

FIELD OF THE INVENTION

This invention relates generally to non-destructive measurement of local material properties. The invention specifically relates to an interferometer useful in determining the thickness and other material properties of thin films.

BACKGROUND OF THE INVENTION

Ultrasound is a common means of nondestructively inspecting materials for flaws and structural integrity. For steels, the preferred frequency used for inspection and sizing of flaws is in the range of 1-10 MHz with 2.25-5 MHz preferred. Pulsed ultrasonic transducers and their electronics, common to the art of nondestructive examination (NDE), are typically relatively broadband, with bandwidth roughly 40% of the nominal operating frequency. Such transducers and electronics are, therefore, ill-suited to interferometry, which requires narrow-band, or "monochromatic", continuous wave "bursts". In addition, the NDE acoustical paths are not critically related to inspection accuracy, except that long paths in metal reduce signal strength due to attenuation. In contrast, interferometry requires well-defined paths of accurate lengths. Therefore, standard methods commonly applied to NDE are not directly applicable to interferometry.

The basic principle behind any interferometer, whether of the acoustical, optical or microwave variety, is linear superposition of waves, i.e., two or more partial waves add algebraically to give the total wave amplitude. This is particularly simple when all of the partial waves have substantially the same frequency. Thus, a monochromatic source is especially desirable to optimize performance of an interferometer.

SUMMARY OF THE INVENTION

The present invention is a method of accurately measuring the thickness of thin films of materials using interference of ultrasonic waves in the frequency range of 2-15 MHz. The ultrasonic interferometer in accordance with the invention produces interference "fringes" that are a function of the film thickness, which fringes are used to determine the thickness. The film may consist of any solid material, metallic or non-metallic, having known sonic properties and a thickness on the order of the sonic wavelength. The choice of frequency is specific to the expected range of film thickness, and there is an inherent minimum thickness that can be measured at any given frequency of ultrasound employed.

The interference effects are also a measure of thin-film material properties other than thickness, e.g., sonic velocity, acoustical impedance, density, elastic modulus, grain size and attenuation coefficient, which can be deduced accurately and repeatably from prepared samples. This allows the material to be characterized locally. Material structure, such as grain size and bonding integrity, can be inferred from data acquired by the interferometer.

The invention employs ultrasonic waveguides in specific geometric relationships to define and control the acoustical path of the interfering waves, thereby creating an instrument with quantitative accuracy and high resolution. The invention further employs an extended, narrow-band ultrasonic source, excited by tone-burst electrical circuitry, to produce a wave packet of nearly monochromatic energy that is capable of producing measurable interference effects when directed along a well-defined and controlled acoustical path. The effectiveness and utility of the device is enhanced by using the narrow-band source of ultrasound in combination with guided-wave propagation to accurately define the acoustical path of the ultrasonic waves producing the interference. This provides greater measurement accuracy than has been possible in the past using broad-band, pulsed devices.

The interferometer of the invention utilizes multi-path and multi-reflection principles to produce an acoustic intensity signal whose properties can be unambiguously interpreted with respect to material property measurements. Thin disks of properly selected materials (e.g., LUCITE TM) are used to refract and partially reflect ultrasonic waves, thereby providing means to divide or "split" the waves to channel them into various legs of a compound waveguide, and to compensate for differences in the acoustical path length for different source frequencies (wavelengths).

Further, a constant-temperature environment is maintained to control thermal effects, such as calibration drifts, thereby assuring accuracy and repeatability of data.

DETAILED DESCRIPTION OF THE PREFERRED EMBODIMENTS

Figure 1:
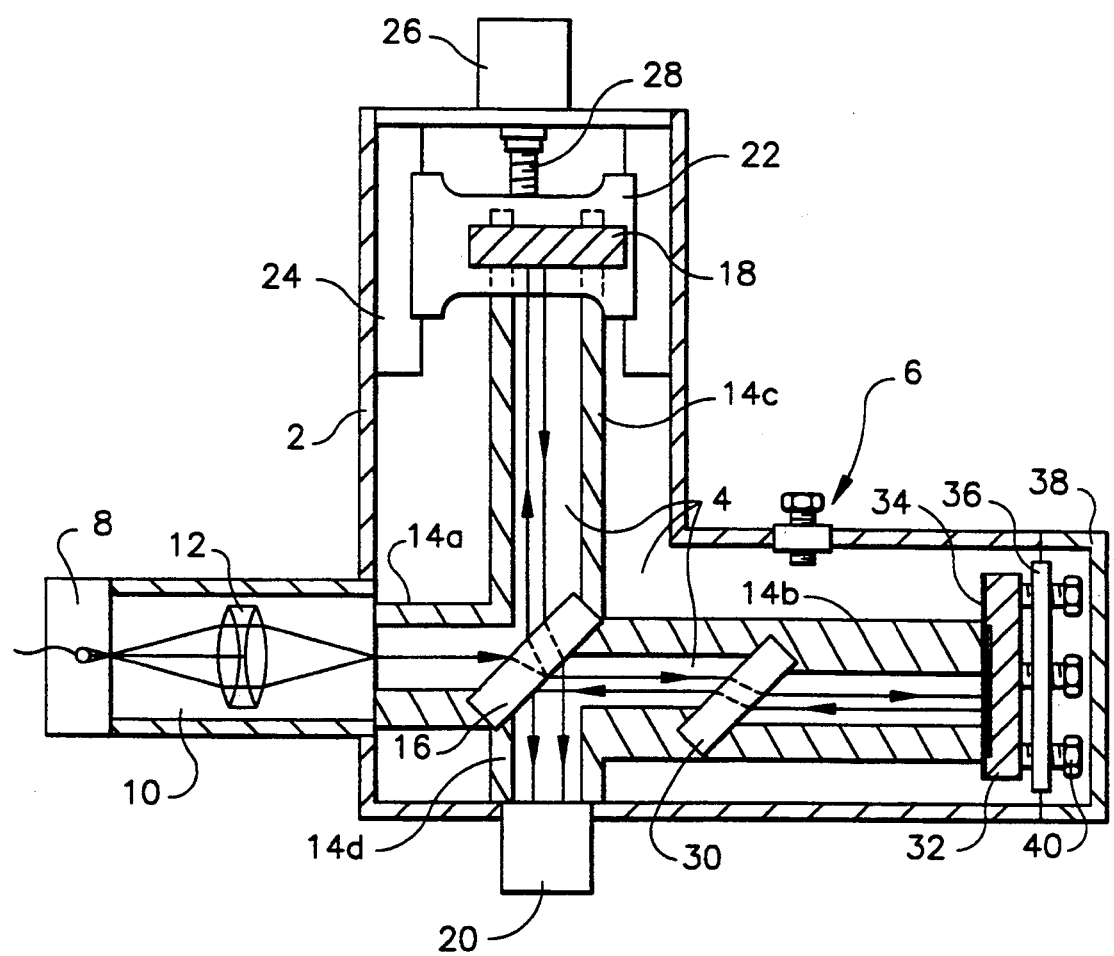
FIG. 1 is a schematic showing the ultrasonic interferometer in accordance with the preferred embodiment of the invention.

To understand the principle of operation of the ultrasonic interferometer in accordance with the invention, consider two waves of frequency $\omega$ propagating in the same direction with amplitudes given by:

$$y_1 = a_1 \sin[\omega t - \alpha_1]; \; y_2 = a_2 \sin[\omega t - \alpha_2] \quad (1)$$

The phase angles $\alpha_1$ and $\alpha_2$ are related to the lengths of their respective propagation (acoustical) paths. The respective amplitudes $a_1$ and $a_2$ are determined by the refractive media in each path. In the case of optical interferometers, these amplitudes are very nearly equal; this is not the case for the ultrasonic interferometer.

The total wave amplitude is:

$$\begin{aligned} y &= y_1 + y_2 = a_1 \sin[\omega t - \alpha_1] + a_2 \sin[\omega t - \alpha_2] \quad (2)\\ &= A \cos[\theta]\sin[\omega t] - A \sin[\theta]\cos[\omega t]\\ &= A \sin[\omega t - \theta] \end{aligned}$$

where:

$$A = (a_1^2 + a_2^2 + 2a_1a_2 \cos[\alpha_1 - \alpha_2])^{\frac{1}{2}} \quad (3)$$

$$\theta = \tan^{-1}\left( \frac{a_1 \sin[\alpha_1] + a_2 \sin[\alpha_2]}{a_1 \cos[\alpha_1] + a_2 \cos[\alpha_2]} \right) \quad (4)$$

Therefore, the total wave has the same frequency, but the amplitude and phase are functions of the amplitudes and phases of the superposed partial waves.

The wave intensity I is proportional to $y^2$, so from Eq. (3):

$$\begin{aligned} I \propto A^2 &= a_1^2 + a_2^2 + 2a_1a_2 \cos[\delta\phi] \\ &= a_1^2 + a_2^2 - 2a_1a_2 + 4a_1a_2 \cos^2[k\,\delta x] \\ &= (a_1 - a_2)^2 + 4a_1a_2 \cos^2[k\,\delta x] \end{aligned} \quad (5)$$

Here, the phase difference $\delta\rho$ and wave number k are related to the change in acoustical path length:

$$\delta\phi = (\alpha_1 - \alpha_2) = 2k\,\delta x; \quad k = \omega/v_p \quad (6)$$

The thickness of the film is $\delta X$ and the phase velocity of ultrasound in the film material is $v_p$. Measurement of the ultrasonic intensity at the output of the interferometer allows a determination of either $\delta X$ or $v_p$, but not both, by virtue of the cosine term in Eq. (5).

For a material film of known thickness, the phase velocity in the material can be measured. Since this is a function of the material properties, such as bulk modulus, the interferometer provides the means of deducing this material property very accurately and locally in a film sample. Furthermore, $a_2$ is a function of attenuation (which varies with frequency) in the sample, as well as known refractive and mode-conversion ratios. It is possible, in principle, to also deduce the attenuation coefficient as a function of frequency using the instrument, although thicker films are required and less accuracy is possible than for purely thickness measurements. These are but a few examples of many potential applications of the device described below.

The ultrasonic interferometer in accordance with the preferred embodiment of the invention is driven by a narrow-band source 8 and has acoustical paths defined by ultrasonic waveguides 14a–14d. The waveguides comprise tubes filled with a viscous, compressible fluid 4, e.g., water, designed for a specific frequency of wave propagation. Since thermal expansion effects can change the acoustical path lengths, the instrument includes a casing 2 which is also filled with fluid 4. The casing is filled via a fill port 6. Fluid 4 is held at constant temperature by conventional temperature control means (not shown).

The narrow-band source 8, driven by "tone-burst" electronics (not shown), produces a wave packet of predetermined length and narrow bandwidth which propagates through couplant 10. The lens system 12 focuses the incident wave packet at the center-line of waveguide 14a. The incident wave packet propagates in waveguide 14a to a splitter 16, where it is first refracted at the front interface and then partially reflected and partially transmitted at the rear interface.

The partially reflected portion forms a reference wave which propagates in waveguide 14c to a movable reflector 18. Reflector 18 reflects the reference wave back to splitter 16, with some of the reference wave being transmitted by splitter 16 toward the ultrasonic detector 20. Reflector 18 is mounted on a carriage 22 that slides along track 24. Carriage 22 displaces in response to rotation of a positioning screw 28 driven by an electronic drive unit 26. The interferometer also comprises conventional means (not shown) for accurately locating the reflector and reading out its relative position electronically.

The portion of the incident wave that is transmitted through splitter 16 is guided by waveguide 14b to a compensator 30. Both the splitter and compensator are plastic plates. The purpose of compensator 30 is to render the acoustical path in plastic of the two ultrasonic waves equal. Compensator 30 also corrects for the fact that the source is not perfectly monochromatic. This is accomplished by placing compensator 30 at a distance from splitter 16 which is selected to produce a standing wave of the desired frequency in the waveguide cavity therebetween. Thus, the compensator and splitter cooperate to act as a very selective frequency filter akin to an optical interference filter.

Figure 2:
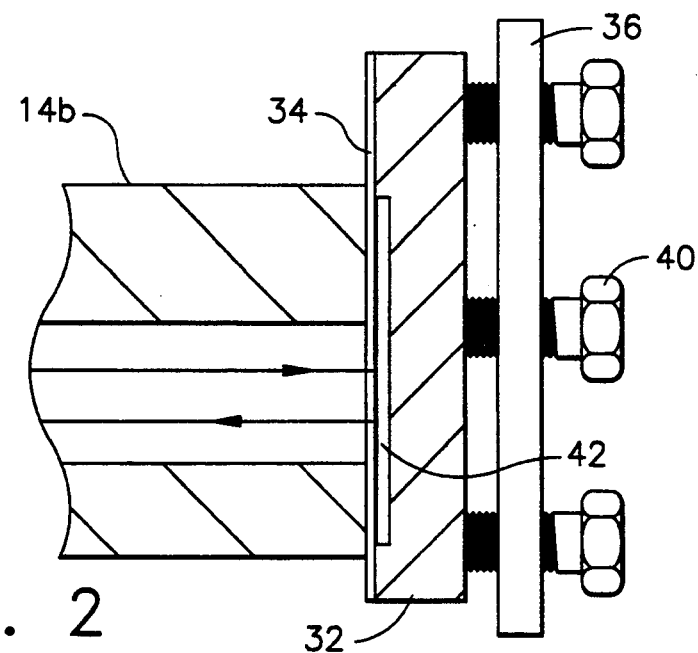
FIG. 2 is a schematic showing on a magnified scale the thin-film sample incorporated in the preferred embodiment of FIG. 1.

The filtered ultrasonic wave then propagates to a substrate 32 with a thin film sample 34 deposited on its front surface. The substrate 32 has a very narrow gas gap 42 (see FIG. 2) machined therein specifically to form a very efficient reflector of ultrasound. The wave impinging on the thin film is partially reflected at the film surface. The remainder of the wave propagates through the film and is totally reflected at the film/gas gap interface. The reflected portions ("echoes") are ultimately partially reflected by splitter 16 and guided to detector 20 by waveguide 14d.

Thus, the first and second echoes returned to splitter 16 by the thin film have phases which are functions of the position of the film surface and the film thickness. The instrument is carefully calibrated using the leveling screws 40 coupled to leveling plate 36 and slide positioning screw 28 to provide destructive interference at the detector due to waveguide acoustical paths. Detector 20 may be either an amplitude detector or an intensity detector of conventional design.

The length of the interferometer leg formed by waveguide 14c is adjusted by incremental movement of carriage 22. The instrument can be calibrated by installing a calibration reflector (not shown) in place of the thin film sample and then determining which setting of carriage 22 and orientation of the calibration reflector produce a null at detector 20. The orientation of the calibration reflector (and the thin-film sample) can be adjusted using leveling screws 40. Then the thin film sample is substituted for the calibration reflector, its position being adjusted such that an ultrasonic wave reflected from the surface of the thin film to detector 20 is 180° out of phase with the wave reflected from reflector 18. The calibration reflector and thin-film sample can be interchanged by removing cap 38 or by installing a rotating head having the calibration reflector and thin-film sample mounted thereon at respective angular positions.

For the case of destructive interference, the only wave detected at detector 20 is due to film penetration by the wave and subsequent reflection at the film/gas gap interface, resulting in the wave phase change of interest. The film thickness can be determined from this phase change coupled with the time-of-flight of the ultrasonic wave reflected at the film surface.

The position of reflector 18 at which the desired interference pattern between its echo and the first echo of the thin film is produced effectively establishes the transit time of the latter. The position of reflector 18 will then be precisely adjusted until the desired interference pattern is produced between the echo from reflector 18 and the second echo from the thin film. Thin film thickness is determined by counting the number of fringes in the monochromatic ultrasonic wave which cross the center of the field of view of the detector 20 during adjustment of reflector 18.

Alternatively, the positions of mirror 18 and the surface of thin film 34 can be adjusted to produce constructive interference, i.e., the ultrasonic wave received at detector 20 is substantially the same as that inputted by the source, disregarding losses along the respective acoustical paths.

Some typical examples of the detected intensity are shown in FIGS. 3–6 for frequencies in the range of 2–15 MHz. The peak-to-peak attenuation is a result of attenuation of the ultrasonic wave as it traverses the film thickness. The attenuation increases with frequency and essentially damps out the higher-order interference effects.

As the frequency of the ultrasonic radiation increases, the intensity oscillations, or "interference fringes", come closer together. Thus, the resolution improves with increasing frequency, allowing increased accuracy. This is a well-known property of interferometry applicable to the present invention, where:

$$2k\,\delta x = m\pi \quad (7)$$

is satisfied for any positive integer m. Peaks occur for m even; valleys result for m odd. Since $k = 2\eta/\lambda$, where $\lambda$ is the ultrasonic wavelength in the film, Eq. (7) amounts to:

$$\delta x = m\lambda/2 \quad (8)$$

for peak-to-peak fringe measurement. For example, in FIG. 5, first-order interference occurs for a film thickness of about 0.27 mm (10.7 mils). Each subsequent peak is an integral multiple of this value. Therefore, the resolution is 0.27 mm at a frequency of 10 MHz. The fringes are separated by half-integer multiples of the ultrasonic wavelength, a known property of other interferometers.

Figure 7:
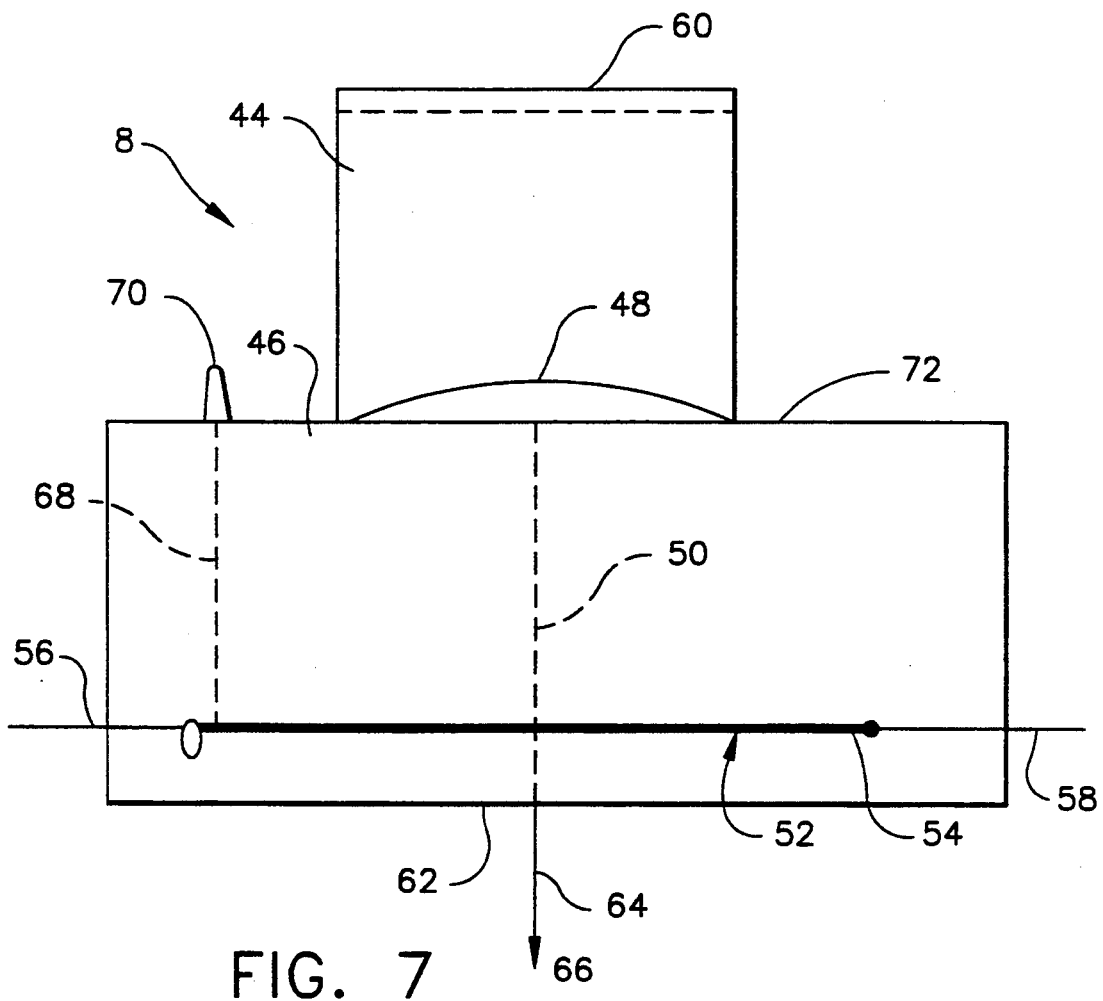
FIG. 7 is a schematic view of a monochromatic ultrasonic transducer incorporated in the preferred embodiment of FIG. 1.
Figure 3:
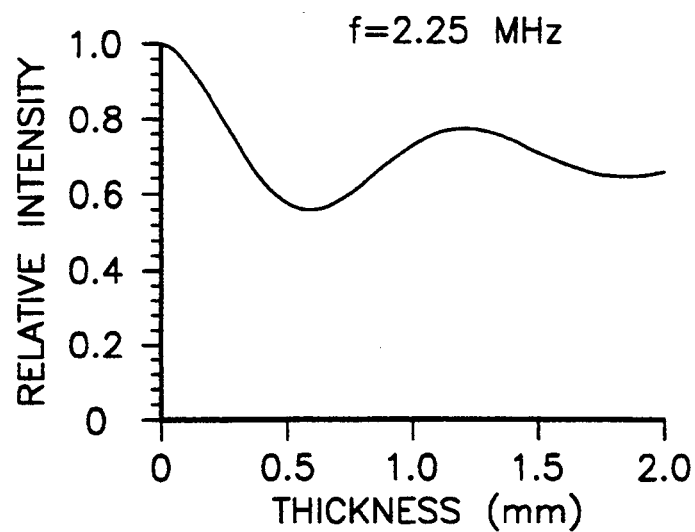
FIGS. 3 through 6 are graphs depicting the relative intensity of the detected ultrasonic waves versus film thickness for frequencies f=2.25, 5, 10 and 15 MHz, respectively.
Figure 4:
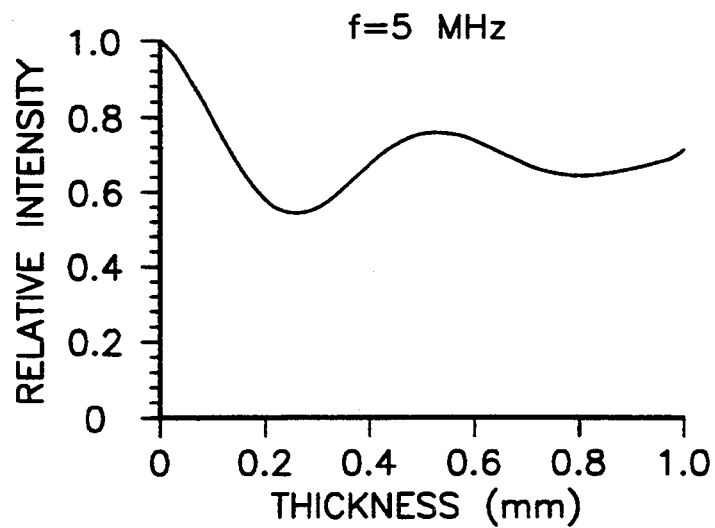
Figure 5:
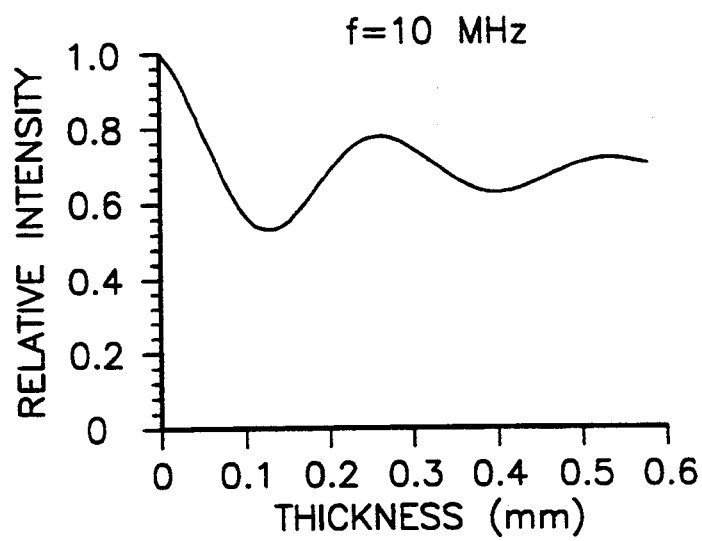
Figure 6:
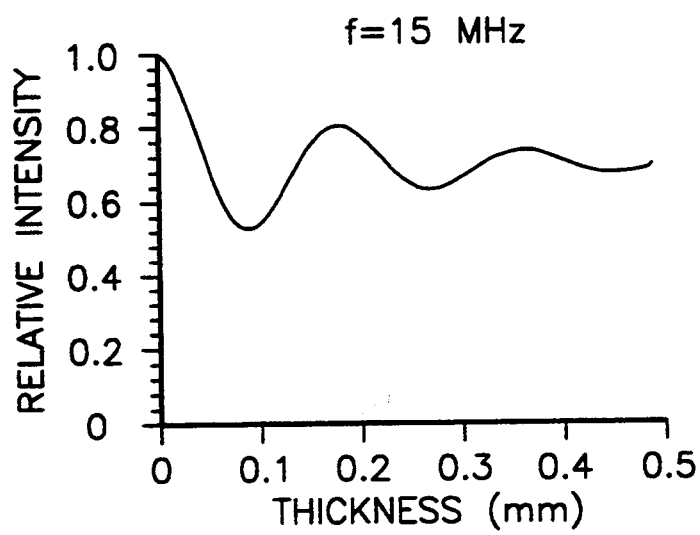

The monochromatic ultrasonic transducer 8, shown in detail in FIG. 7, comprises a piezoelectric crystal 44 mounted on a face 72 of a block 46 (hereinafter "shoe") made of a material having an index of refraction substantially equal to that of the couplant 10. Face 72 is parallel to outer shoe surface 62 and gap 52. The preferred material is an acrylic resin such as LUCITE TM. A convergent lens 48 is arranged between piezoelectric crystal 44 and shoe 46.

The piezoelectric crystal 44 is excited to oscillate by an electrical driving signal imposed at conventional crystal driving means 60 at its design frequency by external drive electronics (not shown). In response to this driving signal, the piezoelectric crystal produces a compressional wave (L-wave) beam. This beam is focused by convergent lens 48 to form a convergent ray bundle 50 propagating in shoe 46.

Shoe 46 is machined to form a very narrow disk-shaped gap 52 of uniform height therein. Although not required, it is desirable that gap 52 be parallel to outer shoe surface 62 to eliminate refraction effects. The disk-shaped cell is out-gassed and back-filled, via a small port 68 and a pinch-off tube 70, with a pure fluid 54. The preferred fluid is water.

The fluid 54 in gap 52 is maintained at a constant temperature by a heater rod 56. The heat output of heater rod 56 is monitored by a thermocouple 58. A controller (not shown) is used to regulate the electric current supplied to the heater element in dependence on the signal received by the thermocouple. The controller is programmed in a conventional manner to maintain the fluid at a constant elevated temperature.

The sonic velocity and the gap width are selected such that a single-mode standing wave is excited resonantly in the gap 52 at the desired frequency, allowing an ultrasonic beam 64 to penetrate the gap unperturbed to impinge upon the outer shoe surface 62.

The ultrasonic beam 64 is transmitted at outer shoe surface 62 to propagate in the direction of ray 66. The transmitted beam contains highly monochromatic energy due to the frequency selectivity of the gap.

The convergent ray bundle 50 incident on the gap 52 will be partially transmitted and partially reflected at the interfaces. This partial transmission and partial reflection will vary with the dimension of the gap 52, the type of fluid therein and the frequency of the sound. For the proper frequency of sound within fluid 54, the partial transmission at one interface of gap 52 constructively interferes with the partial reflection at the opposite interface of the gap, creating a standing wave in the fluid-filled gap. This effect occurs when the gap width is a half-integral number of wavelengths. Thus, the dimensional width of gap 52 is critical. Typically, the gap width is in the range of 0.002 to 0.012 inch, depending on the frequency to be selected. The fluid-filled gap acts as a very selective frequency filter, akin to an optical interference filter.

The foregoing monochromatic ultrasonic transducer is disclosed in U.S. patent application Ser. No. 07/964,998, entitled "Monochromatic Ultrasonic Transducer" and assigned to the assignee of the present application, the disclosure of which is fully incorporated by reference herein.

Further, the ultrasonic waveguides 14a–14d each comprise a flexible tube filled with viscous, compressible fluid. The ultrasonic compressional waves from narrow-band source 8 propagate axially in the fluid. The tube has a wall with an inner surface which is axisymmetric and of constant cross section. The tube may be made of metal, plastic or metal/plastic composite material. Such an ultrasonic waveguide is disclosed in U.S. patent application Ser. No. 07/965,595, entitled "Ultrasonic Waveguide" and assigned to the assignee of the present application, the disclosure of which is fully incorporated by reference herein.

The foregoing preferred embodiment has been disclosed only to illustrate the broad concept of the invention. Variations and modifications of the disclosed preferred embodiment will be readily apparent to practitioners skilled in the art of ultrasonic detection or interferometry. For example, the "legs" of the interferometer are shown in FIG. 1 as being perpendicular, but this is a special case. They can be at any convenient angle, set by design. All such variations and modifications are intended to be encompassed by the claims set forth hereinafter.

I claim:

1. An ultrasonic interferometer comprising:

a source of substantially monochromatic ultrasonic radiation;

means for splitting said substantially monochromatic ultrasonic radiation into a first wave portion which is reflected and a second wave portion which is transmitted;

first reflecting means oriented to reflect said first wave portion back to said splitting means;

second reflecting means positioned to reflect said second wave portion back to said splitting means;

means for detecting a characteristic which is a function of the amplitude of ultrasonic radiation impinging thereon, said detecting means being positioned so that a portion of said first wave portion which is reflected by said first reflecting means and then transmitted by said splitting means and a portion of said second wave portion which is reflected by said second reflecting means and then reflected by said splitting means impinge thereon; and waveguide means for guiding ultrasonic radiation propagating to or from said splitting means, said waveguide means being filled with a viscous, compressible fluid medium.

2. The ultrasonic interferometer as defined in claim 1, wherein said waveguide means comprises first through fourth waveguides for ultrasonically coupling said splitting means with said source, said first reflecting means, said second reflecting means and said detecting means respectively.

3. The ultrasonic interferometer as defined in claim 2, wherein each of said first through fourth waveguides comprises tubular wall means having a channel of substantially constant cross section filled with viscous, compressible fluid.

4. The ultrasonic interferometer as defined in claim 3, wherein said first and third waveguides are mutually parallel, said second and fourth waveguides are mutually parallel and said first and third waveguides are substantially perpendicular to said second and fourth waveguides.

5. The ultrasonic interferometer as defined in claim 2, further comprising second support means which are mounted at an end of said third waveguide such that the orientation of said second support means is adjustable.

6. The ultrasonic interferometer as defined in claim 5, further comprising a thin film of material supported by said second support means, said first reflecting means being a mirror and said second reflecting means being an interface of said thin film and a fluid.

7. The ultrasonic interferometer as defined in claim 6, wherein said second support means has a recess machined into a surface facing said thin film, said recess and said thin film forming an airtight gap filled with said fluid, said second reflecting means being formed by the interface of said thin film and said fluid-filled gap.

8. The ultrasonic interferometer as defined in claim 2, wherein said substantially monochromatic source comprises a piezoelectric crystal, a solid medium having a fluid-filled gap of constant height formed therein, and means for coupling ultrasonic radiation from said piezoelectric crystal into said solid medium.

9. The ultrasonic interferometer as defined in claim 1, further comprising means for compensating for differences in the acoustical path length for different source frequencies, said compensating means being arranged between said splitting means and said second reflecting means.

10. The ultrasonic interferometer as defined in claim 1, further comprising first support means which are slidably displaceable in a direction substantially parallel to the direction of propagation of said first wave portion reflected by said splitting means, said first reflecting means being mounted on said first support means.

11. The ultrasonic interferometer as defined in claim 1, further comprising a casing in which said waveguide means is housed with a cavity therebetween, said cavity and said waveguide means being filled with viscous, compressible fluid.

12. An interferometric method for determining a characteristic of a thin film of material, comprising the steps of:

producing substantially monochromatic ultrasonic radiation;

guiding said substantially monochromatic ultrasonic radiation to propagate through a viscous, compressible fluid to a splitter;

splitting said substantially monochromatic ultrasonic radiation into first and second waves;

guiding said first wave to propagate through said viscous, compressible fluid to a reflector along a first path of known length, said reflector being oriented to reflect said first wave back along said first path;

guiding said second wave to propagate through said viscous, compressible fluid to said thin film along a second path, said thin film being oriented such that first and second interfaces respectively reflect first and second portions of said second wave back along said second path, said first and second interfaces being separated by the thickness of said thin film;

superposing at least a portion of said reflected first wave with said first reflected portion of said second wave by placing said reflector at a first position to produce a first predetermined interference pattern at a detector; and superposing at least a portion of said reflected first wave with said second reflected portion of said second wave by displacing said reflector from said first position to a second position to produce a second predetermined interference pattern at said detector.

13. The interferometric method as defined in claim 12, further comprising the step of counting the number of interference fringes which cross the center of a field of view of said detector during displacement of said reflector from said first position to said second position.

14. The interferometric method as defined in claim 12, wherein said wave of substantially monochromatic ultrasonic radiation is produced by transmitting ultrasonic radiation through a fluid-filled gap having a height which is a function of the desired frequency of said wave of substantially monochromatic ultrasonic radiation.

15. The interferometric method as defined in claim 12, further comprising the step of compensating for differences in the acoustical path length for different source frequencies.

16. The interferometric method as defined in claim 12, wherein said second interface comprises an interface between said thin film and a fluid medium.

17. The interferometric method as defined in claim 12, further comprising the step of maintaining the temperature of said viscous, compressible fluid substantially constant.

18. An ultrasonic interferometer comprising:
a source of substantially monochromatic ultrasonic radiation;
means for splitting said substantially monochromatic ultrasonic radiation into a first wave which is reflected and a second wave which is transmitted;
first support means which are slidably displaceable in a direction substantially parallel to the direction of propagation of said first wave;
reflecting means mounted on said first support means and oriented to reflect said first wave back to said splitting means;
second support means which can be adjustably oriented;
a thin film of material mounted on said second support means and positioned such that a first interface of said thin film and a first fluid and a second interface of said thin film and a second fluid respectively reflect first and second portions of said second wave back to said splitting means;
means for detecting a characteristic which is a function of the amplitude of the ultrasonic radiation impinging thereon, said detecting means being positioned so that a portion of said first wave which is reflected by said reflecting means and then transmitted by said splitting means and a portion of said second wave which is reflected by said second interface and then reflected by said splitting means impinge thereon; and
waveguide means for guiding ultrasonic radiation propagating to or from said splitting means, said waveguide means being filled with a viscous, compressible fluid medium.

19. The ultrasonic interferometer as defined in claim 18, wherein said first interface comprises an interface between said thin film and said viscous, compressible fluid and said second interface comprises an interface between said thin film and a fluid-filled gap between said thin film and said second support means.

20. The ultrasonic interferometer as defined in claim 18, wherein said substantially monochromatic source comprises a piezoelectric crystal, a solid medium having a fluid-filled gap of constant height formed therein, and means for coupling ultrasonic radiation from said piezoelectric crystal into said solid medium.

* * * * *